(12) United States Patent
Obuz (10) Patent No.: US 8,235,036 B2
(45) Date of Patent: Aug. 7, 2012

(54) PORTABLE UNIVERSAL INHALER SYSTEM (75) Inventor: Vedat Obuz, Merion Station, PA (US)

(73) Assignee: Vedat Obuz, Merion Station, PA (US)

( * ) Notice: Subject to any disclaimer, the term of this patent is extended or adjusted under 35 U.S.C. 154(b) by 1852 days.

(21) Appl. No.: 11/223,625

(22) Filed: Sep. 9, 2005

(65) Prior Publication Data
US 2007/0056581 A1 Mar. 15, 2007

(51) Int. Cl.
A61M 11/00 (2006.01)
A61M 16/00 (2006.01)
A61M 15/08 (2006.01)

(52) U.S. Cl. ......... 128/200.14; 128/200.18; 128/200.23; 128/200.24; 128/203.23

(58) Field of Classification Search ............ 128/200.14, 128/200.18, 200.23, 200.24, 203.23
See application file for complete search history.

(56) References Cited

U.S. PATENT DOCUMENTS

| 4,130,116 | A | * | 12/1978 | Cavazza | 128/200.23 |
|---|---|---|---|---|---|
| 5,042,467 | A | | 8/1991 | Foley | |
| 5,564,414 | A | * | 10/1996 | Walker et al. | 128/200.23 |
| 5,645,049 | A | | 7/1997 | Foley et al. | |
| 5,730,118 | A | * | 3/1998 | Hermanson | 128/200.14 |
| 5,755,218 | A | * | 5/1998 | Johansson et al. | 128/200.14 |
| 5,848,588 | A | | 12/1998 | Foley et al. | |
| 5,855,202 | A | | 1/1999 | Andrade | |
| 5,988,160 | A | | 11/1999 | Foley et al. | |
| 6,293,279 | B1 | | 9/2001 | Schmidt et al. | |
| 6,345,617 | B1 | | 2/2002 | Engelbret et al. | |
| 6,435,177 | B1 | | 8/2002 | Schmidt et al. | |
| 6,523,536 | B2 | | 2/2003 | Fugelsang et al. | |
| 6,698,422 | B2 | | 3/2004 | Fugelsang et al. | |
| 6,886,560 | B1 | * | 5/2005 | Seppala | 128/203.15 |
| 6,892,728 | B2 | * | 5/2005 | Helgesson et al. | 128/203.15 |
| 7,063,686 | B2 | * | 6/2006 | Mezzoli | 604/275 |
| 2005/0268908 | A1 | * | 12/2005 | Bonney et al. | 128/203.15 |

OTHER PUBLICATIONS

*Using an Aerochamber® with a Mask for your Inhaled Asthma Medication*, National Jewish Medical and Research Center, © 2003, Online, Retrieved on Jun. 20, 2005, Retrieved from the internet: http://asthma.nationaljewish.org/treatments/devices/aerochamber_mask.php, pp. 1-2.

(Continued)

*Primary Examiner* — Patricia Bianco
*Assistant Examiner* — Nihir Patel
(74) *Attorney, Agent, or Firm* — Knoble Yoshida & Dunleavy, LLC (57) ABSTRACT

A portable universal inhaler system formed from an outer part and an inner part slidably received in the outer part. The inner part defines a compartment for receiving a medication canister and includes a universal connector for making a fluid dispensing connection to a variety of commercially available canisters. The inner and outer parts, when assembled, together form a housing that defines a chamber of sufficient volume to house a metered dose of medication. A mouthpiece or mouthpiece attachment location is provided in fluid communication with the chamber for permitting inhalation of medication from the chamber. The structure of the device makes it compact and portable, in the closed position, allows for storage of a medication canister in operative engagement with the device, and provides a convenient way to dispense medication, using a medication canister and a chamber, for inhalation by a user.

20 Claims, 5 Drawing Sheets

OTHER PUBLICATIONS

*PDR Drug Information for AeroChamber Plus and AeroChamber Plus with Mask*, Drugs.com Drug Information Online, © 2005, Online, Retrieved on Jun. 20, 2005, Retrieved from the internet: http://www.drugs.com/PDR/AeroChamber_Plus_and_Aero_Chamber_Plus_with_Mask.html, pp. 1-12.

*Asthma COPD Products AeorChamber Plus\* Valved Holding Chmaber ("VHC") with Adult Mouthpiece*, Trudell Medical International, © 1997-2001, Online, Retrieved on Jun. 20, 2005, Retrieved from the internet: http://www.trudellmed.com/copd_aerochamberplus_vhc_adult.shtml, pp. 1-2.

*Why use an AeroChamber Plus\* Valved Holding Chamber?*, Trudell Medical International, © 1997-2001, Online, Retrieved on Jun. 20, 2005, Retrieved from the internet: http://www.trudellmed.com/copd_aerochamberplus_vhc_adult_why_use.shtml, pp. 1-2.

*Asthma COPD Products Wide Range of Formulations*, Trudell Medical International, © 1997-2001, Online, Retrieved on Jun. 20, 2005, Retrieved from the internet: http://www.trudellmed.com/copd_range_of_formulations.shtml, pp. 1-4.

Forest Laboratories, Inc., *Directions for Use for AeroChamber Plus Valved Holding Chamber with FLOWSIGnal® Whistle with ComfortSeal® Mask*, 2001,2005 ©.

Forest Laboratories, Inc., *Directions for Use for AeroChamber Plus Valved Holding Chamber with ComfortSeal® Mask*, 2001,2005 ©.

*Allergy and Asthma in the Southwestern United States, Three E-Z Spacers\*, one collapsed, two with inhaler canisters attached*, The University of Arizona Health Science Center, Online, Retrieved on Jun. 20, 2005, Retrieved from the internet: http://allergy.peds.arizona.edu/southwest/devices/spacers/ezspacer.htm, p. 1.

*Using an E-Z Spacer® for Your Inhaled Asthma Medication*, National Jewish Medical and Research Center, © 2003, Online, Retrieved on Jun. 20, 2005, Retrieved from the internet: http://asthma.nationaljewish.org/treatment.devices/ez_spacer.php, pp. 1-2.

*EZ Spacer Drug Delivery System*, Allergy Be Gone, Online, Retrieved Jun. 21, 2005, Retrieved from the internet: http//www.allergybegone.com/ezspacerdrugde.html, p. 1.

*Allergy and Asthma in the Southwestern United States, Inspirease\* with Ventolin Canister*, The University of Arizona Health Sciences Center, ©, Online, Retrieved on Jun. 20, 2005, Retrieved from the internet: http://allergy.peds.arizona.edu/southwest/devices/spacers/inspirease.htm, p. 1.

*Using an InspiEase® Spacer for Your Inhaled Asthma Medication*, National Jewish Medical and Research Center, © 2003, Online, Retrieved on Jun. 21, 2005, Retrieved from the internet: http//asthma.nationaljewish.org/treatments/devices/inspirease.php, pp. 1-2.

*How to Use a Metered Dose Inhaler with Inspirease Spacer*, The Cleveland Clinic, Online, Retrieved on Jun. 21, 2005, Retrieved from the internet: http://www.clevelandclinic.org/health-info/docs/0300/0357.asp?index=4304&src=news, p. 1-2.

*Inspirease® Starter Kit*, Allergy Asthma Technology Ltd., © Allergy Asthma Technology Ltd., Online, Retrieved on Jun. 21, 2005, Retrieved from the internet: http://www.allergyasthmatech.com/allergyasthmatech/product-detail.asp?ItemID=243, p. 1.

*Metered-Dose Inhaler (MDI) Used with an InspirEase Spacer*, University of Michigan Health System, © 2004, Online, Retrieved on Jun. 21, 2005, Retrieved from the internet: http://www.med.umich.edu/1libr/pa/pa_mdinspir_hhg.htm, p. 1.

*Metered-Dose Inhaler (MDI) with InspirEase®*, Cincinnati Children's Hospital Medical Center, © 1999-2005, Online, Retrieved on Jun. 21, 2005, Retrieved from the internet: http://www.cincinnatichildrens.org/health/info/allergy-asthma/home/inspirease.htm, pp. 1-2.

*Instructions for Use of InspirEase*, Pulmonary Allergy & Critical Care Medicine, Online, Retrieved on Jun. 21, 2005, Retrieved from the internet: http://www.umassmed.edu/pulmonary/inspirease.cfm, p. 1.

*Metere-Dose Inhaler (MDI) Used with an InspirEase Spacer*, Allina Hospitals and Clinics, © 2004, Online, Retrieved on Jun. 21, 2005, Retrieved from the internet: http://www.medformation.com/ac/crspa.nsf/file/crs-pa-hhg_mdi.with.inspirease, pp. 1-2.

*Lab Supplies Products Category List: Flowmeters*, Omega Bio-Tek, © 2001, Online, Retrieved on Jun. 21, 2005, Retrieved from the internet: http://www.omegabiotek.com/supplyweb/flowmeters.htm, pp. 1-5.

*Allergy and Asthma in the Southwestern United States, Ace\* Spacer*, The University of Arizona Health Science Center, Online, Retrieved on Jun. 20, 2005, Retrieved from the internet: http://allergy.peds.arizona.edu/southwest/devices/spacers/ace_spacer.htm, p. 1.

Hugh D.C. Smyth, Vance P. Beck, Dennis Williams, and Anthony J. Hickey, *The Influence of Formulation and Spacer Device on the in Vitro Performance of Solution Chlorofluorocarbon-Free Propellant-Driven Metered Dose Inhalers*, A publication of the American Associate of Pharmeceutical Scientists, © 2003, aaps PharmSciTech, Online, Retrieved on Jun. 21, 2005, Retrieved on the internet: http://www.aapspharmscitech.org/view.asp?art=pt050107&pdf=yes, pp. 1-10.

Dr. Shailaja Somaraju, *Optimizing Pulmonary Drug Delivery Using Spacer Devices in Conjunction with Pressurized Metered Dose Inhalers*, University of Maryland School of Pharmacy, © 1994-2002, Online, Retrieved on Jun. 21, 2005, Retrieved on the internet: http://www.pharmacy.umaryland.edu/faculty/rdalby/Research%20Web%20Pages/Shailaja_Somaraju.htm, pp. 1-2.

Michael J. Asmus, Pharm., D., Judy Liang, Pharm D., Intira Coowanitwong, Ph.D. and Günther Hochhaus, Ph.D., *In Vitro Performance Characteristics of Valved Holding Chamber and Spacer Devices with a Fluticasone Metered-Dose Inhaler*, accp American College of Clinical Pharmacy, Pharmacotherapy 2004;24(2):159-294, Online, Retrieved Jun. 21, 2005, Retrieved on the internet: http://www.accp.com/pharmacotherapy/pharm2402.php, pp. 1-9.

Allergy and Asthma in the Southern United States, Ellipse spacer with Ventolin inhaler, The University of Arizona Health Sciences, Online, Retrieved on Jun. 20, 2005, Retrieved on the internet: http://allergy.peds.arizona.edu/southwest/devices/spacers/ellipse.htm, p. 1.

Williams RO 3rd, Patel AM, Barron MK, Rogers TL, *Investigation of some commercially available spacer devices for the delivery of glucocorticoid steroids from a pMDI*, Drug Dev Ind Pharm. May 2001; 27(5):401-12.

Michael J. Asmus, Pharm., D., Judy Liang, Pharm D., Intira Coowanitwong, Ph.D. and Günther Hochhaus, Ph.D., *In Vitro Performance Characteristics of Valved Holding Chamber and Spacer Devices with a Fluticasone Metered-Dose Inhaler*, accp American College of Clinical Pharmacy, Pharmacotherapy 2004;24(2):159-166, Online, Retrieved Jun. 21, 2005, Retrieved on the internet: http://www.medscape.com/viewarticle/468791, pp. 1-2.

*Inhaled Asthma Medication With a Metered-Dose Inhaler (MDI) and Spacer*, National Jewish Medical and Research Center, 2003, Online, Retrieved on Jun. 21, 2005, Retrieved on the internet: http://asthma.nationaljewish.org/treatments/devices/metered_spacer.php, p. 1.

Ronald W. England, Jeffrey S. Nugent, Kurt W. Grantwohl, Larry Hagan, James M. Quinn, *High-Dose Inhaled Fluticasone and Delayed Hypertensity Skin Testing*, © 2003 American College of Chest Physicians, Chest 2003;123:1014-1017.

*Inhaled Steroids*, Allergy & Asthma Disease Management Center, © 1997-2005 American Academy of Allery, Asthma & Immunology, Online, Retrieved on Jun. 21, 2005, Retrieved on the Internet: http://www.aaaai.org/aadmc/ate/inhaledsteroids.html, pp. 1-21.

Allergy and Asthma in the Southern United States, Optichamber* with Ventolin inhaler, The University of Arizona Health Sciences, Online, Retrieved on Jun. 20, 2005, Retrieved on the Internet: http://allergy.peds.arizona.edu/southwest/devices/spacers/optichamber.htm, p. 1.

*OptiChamber Advantage Valved Holding Chamber*, Allergy Be Gone, Online, Retrieved Jun. 21, 2005, Retrieved from the Internet: http//www.allergybegone.com/opvahoch10pe.html, pp. 1-2.

*Optichamber™*, Allergy Asthma Technology Ltd., © Allergy Asthma Technology Ltd., Online, Retrieved on Jun. 21, 2005, Retrieved from the internet: http://www.allergyasthmatech.com/allergyasthmatech/product-detail.asp?ItemID=233, p. 1.

*Valved Holding Chamber for Use With Metered Dose Inhalers (MDI)*, OptiChamber® Advantage, Online, Retrieved on Jun. 21, 2005, Retrieved from the Internet: http://www.autocontrol.com/products/respiratory/respironics.jsp?id-optichamber.

*OptiChamber Advantage Valved Holding Chamber*, National Allergy Supply Incorporated, © 1996-2005, Online, Retrieved on Jun. 21, 2005, Retrieved from the internet: http://natlallergy.com/allergy_relief/1556/optichamber-advantage-mdi-spacer-holding-chamber.html, p. 1.

*OptiChamber*, DRE Veteranary, © 2003, Online, Retrieved on Jun. 21, 2005, Retrieved on the Internet: http://www.dremed.com/vetlab/index.php/cPath/205_425, pp. 1-2.

*OptiChamber Valved Holding Chamber*, PriceGrabber.com, Online, Retrieved on Jun. 21, 2005, Retrieved from the internet: http://www.pricegrabber.com/search_getprod.php.masterid=4731063/, p. 1.

*OptiChamber® Advantage Valved Holding Chamber—Optichamber Hold Chamber 1*, MedShop Express, © 2002-2003, Online, Retrieved on Jun. 21, 2005, Retrieved from the Internet: http://shop.store.yahoo.com/physlabs/20203556.html, pp. 1-2.

*Allergy and Asthma in the Southwestern United States, Spacer Devices for Metered Dose Asthma Inhalers*, The University of Arizona Health Sciences Center, © 2004, Online, Retrieved on Jun. 20, 2005, Retrieved on the internet: http://allergy.peds.arizona.edu/southwest/devices/spacers/spacer.html, pp. 1-2.

*Allergy and Asthma in the Southwestern United States, Aerochambers with and without masks*, The University of Arizona Health Sciences Center, Online, Retrieved on Jun. 20, 2005, Retrieved from the internet: http://allergy.peds.arizona.edu/southwest/devices/spacers/aerochamber.htm, p. 1.

*Metered-Dose Inhaler Used with an Aerochamber*, University of Michigan Health System, © 2004, Online, Retrieved on Jun. 20, 2005, Retrieved from the internet: http://www.med.urnich.edu/1libr/pa/pa_mdaeroch_hhg.htm, pp. 1-2.

*Metered-Dose Inhaler with AeroChamber®*, Cincinnati Childrens Hospital Medical Center, © 199-2005, Online, Retrieved on Jun. 20, 2005, Retrieved from the internet: http://www.cincinnatichildrens.org/health/info/allergy-asthma/home/aerochamber.htm, pp. 1-2.

*AeroChamber Plus—Product Information*, Forest Pharmaceuticals, Inc., © 2005, Online, Retrieved on Jun. 20, 2005, Retrieved from the internet: http://www.aerochambervhc.com/patient/default.asp, p. 1.

*AeroChamber Plus—Frequently Asked Questions*, Forest Pharmaceuticals, Inc., © 2005, Online, Retrieved on Jun. 20, 2005, Retrieved from the internet: http://www.aerochambervhc.com/patient/faq.asp.

*AeroChamber Plus Valved Holding Chamber, to maximize the delievery of medication into the lungs*, Forest Laboratories, © 2005, Online, Retrieved on Jun. 20, 2005, Retrieved from the Internet: http://www.frx.com/products/aerochamber.aspx, p. 1.

*OptiHaler® for Asthmatics*, The University of Arizona Health Sciences Center, Online, Retrieved on Jun. 20, 2005, Retrieved from the internet: http://rx.health.arizona.edu/optihaler.htm, p. 1.

*Metered-Dose Inhaler with Optihaler®*, Cincinnati Children's Hospital Medical Center, © 1999-2005, Online, Retrieved on Jun. 20, 2005, Retrieved from the internet: http://www.cincinnatichildrens.org/health/info/allergy-asthma/home/optihaler.htm, pp. 1-2.

*OptiHaler Metered Dose Inhaler, Dynamic Mixing Action Gives you the most from MDI Medications*, National Allerfy Supply, Inc., © 1996-2005, Online, Retrieved on Jun. 20, 2005, Retrieved from the internet: http://www.natlallergy.com, p. 1.

*OptiHaler™ Drug Delivery System*, Allergy Asthma Technology Ltd., ©, Online, Retrieved on Jun. 20, 2005, Retrieved from the internet: http://a;;ergyasthmatech.com/allergyasthmatech/productdetailo.asp?ItemID=242, p. 1.

*OptiHaler*, Online, Retrieved on Jun. 20, 2005, Retrieved from the internet: http://maxshouse.com/optihaler.htm, pp. 1-2.

Optihaler® Aerosol Drug Delivery System, The Medical Supply Company, Inc., © 1998-2004, Online, Retrieved on Jun. 20, 2005, Retrieved from the internet: http://www.medsupplyco.com/Products/Product Details.cfm/ProductNumber/HDN765, p. 1.

\* cited by examiner

PORTABLE UNIVERSAL INHALER SYSTEM

FIELD OF THE INVENTION

The present invention relates to a portable universal inhaler system for effectively delivering medications by inhalation through the mouth. More specifically, the present invention relates to a portable inhaler system that can be used with a variety of different medication canisters.

BACKGROUND OF THE INVENTION

The delivery of a metered dose of medication via inhalation into the lungs is a common method used for administration of a variety of drugs, including, but not limited to, asthma medications, insulin, steroids and treatments for pulmonary diseases. Although the metered dose inhaler canister dispenses a fixed, metered dose of medication, only a portion of the metered dose actually reaches the lungs of a patient. Even if inhalation is properly timed with the dispensing of the medication from the inhaler, the amount of medication reaching the lungs is inconsistent, depending on various factors including the quantity of medication dissolved and/or entrained in the air entering the patient's lungs, and the quantity of medication that is deposited on one or more surfaces of the inhaler, the mouth and/or oropharyngeal area of the patient. Deposition of medication in the mouth or oropharyngeal area of the patient can cause complications, such as candidiasis, and may leave an unpleasant aftertaste.

Many patients also have practical problems with the use of inhalers, such as difficulty compressing the dose canister, difficulty in timing inhalation with the dispensing of medication, and an inability to inhale a full dose of medication in a single breath. In practice, patients frequently activate an inhaler multiple times in order to dispense a single dose, despite the fact that the desired metered dose should have been dispensed via a single activation of the inhaler. This is a documented response to the difficulty and inconsistency of medication delivery, which response undermines the effectiveness of metered dose inhalers, thereby leading to concerns such as over-medication, under-medication, and waste, as well as higher costs for treatment. The problem with improper storage and difficulty with sterilization techniques also poses risk for further unwanted fungal and bacterial infections.

One proposed solution to the problem of inconsistent dosing has been to provide a "spacer" or "chamber" within the inhalation device, typically in the form of a reservoir of air. The spacer or chamber provides a location for mixing the metered dose of medication with air before inhalation, thereby potentially reducing the inconsistency of dosing due to timing difficulties. U.S. Pat. Nos. 4,470,412; 4,790,305; 4,926,852; 5,012,803; 5,040,527; 5,042,467; 5,816,240; and 6,026,807 disclose various devices of this type.

Additionally, some devices with spacers have been provided with a valve mechanism to permit inhalation of a single dose of medication in more than one breath. For example, see U.S. Pat. Nos. 4,470,412 and 5,385,140. The articles, Demirkan, et al., "Salmeterol Administration by Metered-Dose Inhaler Alone vs. Metered-Dose Inhaler Plus Valved Holding Chamber," Chest, 117 (2000) pp. 1314-1318, Finlay and Zuberbuhler, "In vitro comparison of beclomethasone and salbutamol metered-dose inhaler aerosols inhaled during pediatric tidal breathing from four valved holding chambers," Chest, 114 (1998) pp. 1676-1680, and Konig, "Spacer devices used with metered-dose inhalers. Breakthrough or gimmick?" Chest, 88 (1985) pp. 276-284; also provide information in relation to such devices.

For infants or other patients who have difficulty using a mouthpiece, a mask is commonly attached or incorporated onto the inhaler. See U.S. Pat. Nos. 4,809,692; 4,832,015; 5,012,804; 5,427,089; 5,645,049 and 5,988,160. Also, some devices include an audible signaling device to warn patients when inhalation exceeds a desirable rate, e.g. U.S. Pat. Nos. 4,809,692 and 5,042,467.

One method of attaching a spacer to a canister of a metered dose inhaler is to insert the inhaler into a universal adapter such as that shown in U.S. Pat. No. 5,848,588, but this is bulky and awkward to use. Other devices are designed to have a specific canister inserted into the device. It would be beneficial to be able to insert different canisters into a single inhaler.

Accordingly, in view of the foregoing, there remains a need for an easily portable, universal inhaler system that can be easily used and cleaned. There is also a need for a design that permits the use of attachments for infants, if desired. These and other objects of various embodiments of the invention are addressed by one or more of the embodiments of the invention described below. It should be understood, however, that specific embodiments of the invention need not address each and every object listed herein in order to be considered part of the inventive concept.

SUMMARY OF THE INVENTION

In one aspect, the present invention relates to an inhaler system that includes structure that permits insertion of different medication canisters.

In another aspect, the present invention relates to an inhaler system that is easily portable and includes structure that permits insertion of different medication canisters. In this aspect, the inhaler system includes at least two parts, one of which parts fits at least partially within another part to thereby enhance the portability of the device.

In another aspect, the present invention relates to an inhaler system that can be easily cleaned and/or sterilized. In this aspect, the inhaler system includes two or more parts that can be readily disassembled and reassembled to allow thorough cleaning or sterilization of the surfaces of the device.

BRIEF DESCRIPTION OF THE DRAWINGS

For the purpose of illustrating the invention, representative embodiments are shown in the accompanying figures, it being understood that the invention is not intended to be limited to the precise arrangements and instrumentalities shown.

DETAILED DESCRIPTION OF THE PREFERRED EMBODIMENTS

Figure 1:
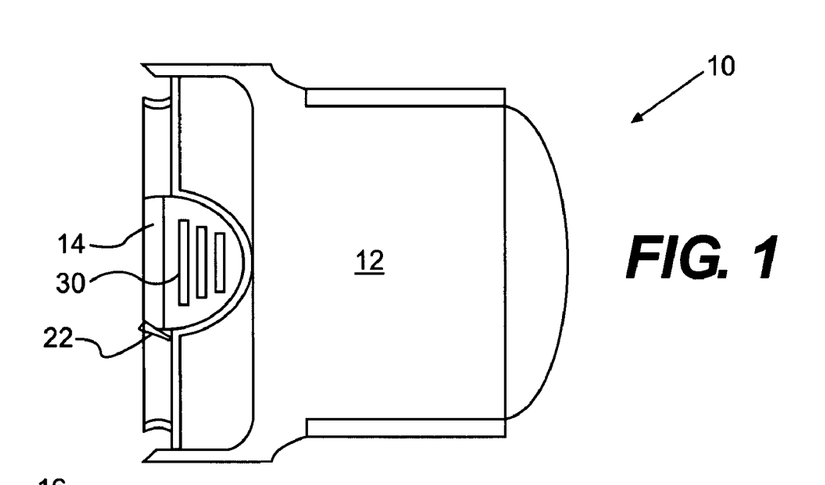
FIG. 1 is a top view of one embodiment of an inhaler system of the present invention, in the closed position.
Figure 2:
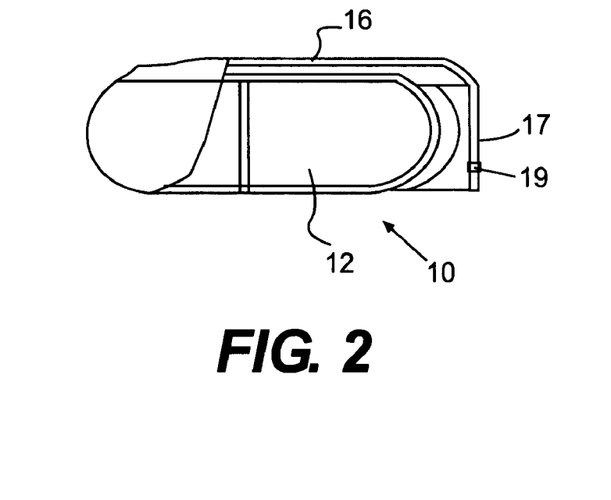
FIG. 2 is a side view of the inhaler system of FIG. 1 in the closed position.
Figure 3:
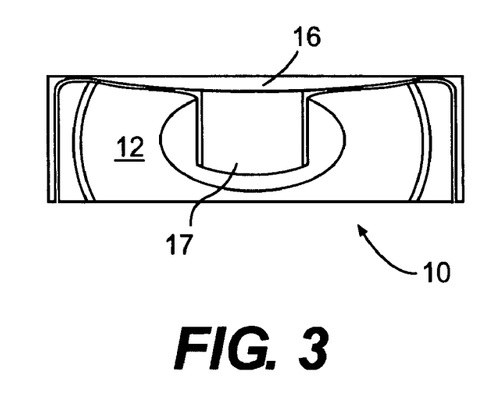
FIG. 3 is an end view of the inhaler system of FIG. 1 in the closed position.

Referring to FIGS. 1-3, there is shown an embodiment of an inhaler system 10 in accordance with the present invention, depicted in the closed position. The closed position of inhaler system 10 is designed for storage and transport of the inhaler system 10. In the closed position of FIGS. 1-3, the inhaler system is relatively small and can fit, for example, into a clothing pocket for storage or transport. Moreover, in this closed position, the inhaler system 10 houses at least one medication canister therein, thereby eliminating the need to carry a medication canister separately from system 10.

In FIG. 1, is shown a top view of inhaler system 10 in the closed position. Inhaler system 10 includes an outer part 12 and an inner part 14, which together form a housing. Inner part 14 is sized to fit within outer part 12, optionally with a friction-fit, form fit or another type of fit that creates a seal between inner part 14 and outer part 12 to provide a substantially airtight chamber 18 within outer and inner parts 12, 14, when they are fitted together in at least the open position.

Inner part 14 includes a canister compartment 20 into which a canister can be inserted. Canister compartment 20 is adapted to be substantially universal in that it is designed to accept canisters of different sizes and lengths. Tapered opening 22 of compartment 20 facilitates insertion and removal of different sized canisters into compartment 20 of inner part 14, by providing an area from which the canister can protrude outwardly from compartment 20. Since tapered opening 22 is tapered, as shown, compartment 20 can accommodate canisters of different lengths, while still permitting the user to depress the canister within compartment 20 in order to dispense a metered dose of medication from the canister. Compartment 20 is sized to have a diameter which accommodates one of the widest, if not the widest, of the commercially available canisters so that canisters of smaller diameters can also be fit into compartment 20 of inner part 14.

FIG. 2 depicts a side view of the inhaler system 10 of FIG. 1 in a closed position. In FIG. 2, cover 16 of inhaler system 10 is shown. Cover 16 provides a convenient way to close inhaler system 10 and may also be employed to retain outer and inner parts 12, 14 together in both the open and closed positions. The inner surface 24 of cover 16 is a convenient location to provide product information, product literature, and/or instructions for use of inhaler system 10. Cover 16 may also be provided with a grasping structure 19 for facilitating grasping of cover 16 by the user to open and close cover 16. Any suitable, conventional grasping structure may be employed.

Figure 4:
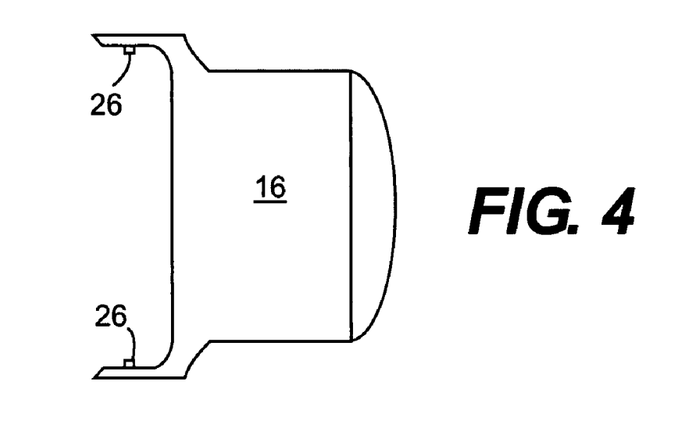
FIGS. 4-6 are top, side and end views, respectively, of the cover of the inhaler system of FIGS. 1-3.
Figure 5:
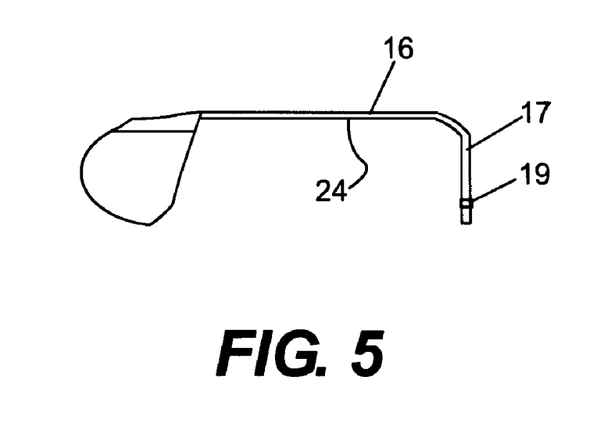
Figure 6:
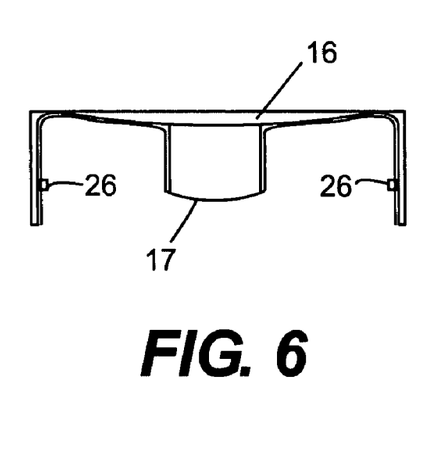

FIG. 3 shows an end view of inhaler system 10 of FIG. 1 in a closed position. From this view, it can be seen that cover 16 includes a tab 17 that extends down and over a portion of the end of inhaler system 10. The purpose of tab 17 is to cover mouthpiece 40 of inner part 14. Referring to FIGS. 4-6, three different views of cover 16 are shown, with these views corresponding to the views of the inhaler system 10 seen in FIGS. 1-3. In FIGS. 4 and 6, it can be seen that cover 16 may include a two pegs 26 which are designed to fit into corresponding recesses 28 in outer part 12. In this manner, cover 16 can be releasably secured to outer part 12 by locating pegs 26 in recesses 28. Also, this manner of mounting cover 16 to outer part 12 permits cover 16 to pivot about pegs 26 to permit opening and closing of the cover 16, as shown, without removing the cover 16 from the outer part 12. Any other suitable, conventional structure for mounting cover 16 onto outer part 12 may be employed, so long as cover 16 can be easily removed from outer part 12 to permit cleaning of the inhaler system 10, and cover 16 can pivot about an axis located approximately between the locations of pegs 26 of cover 16, relative to outer part 12, to allow opening and closing of cover 16.

Figure 7:
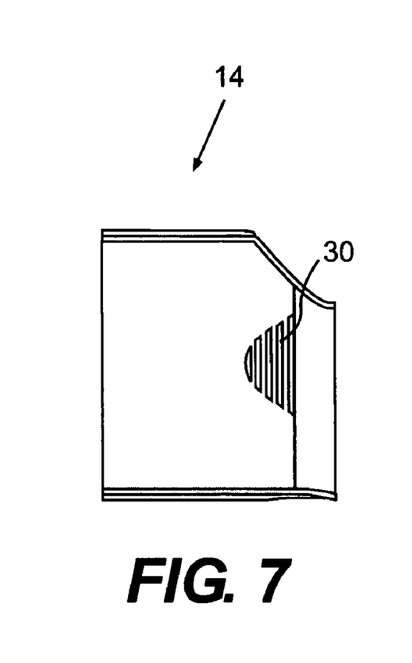
FIG. 7 is a top view of the inner part of the inhaler system shown in FIGS. 1-3.
Figure 8:
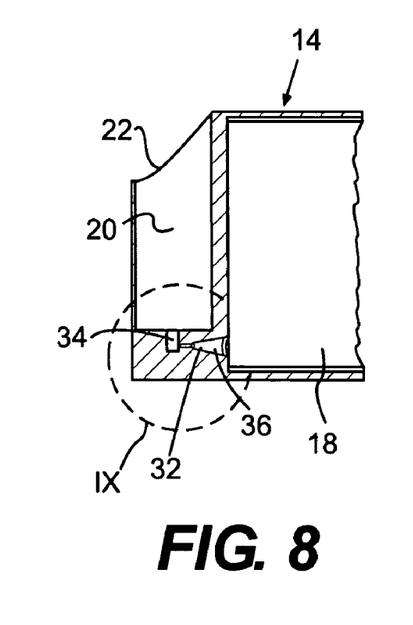
FIG. 8 is a cross-sectional view of a portion of the inner part of the inhaler system of FIGS. 1-3.
Figure 9:
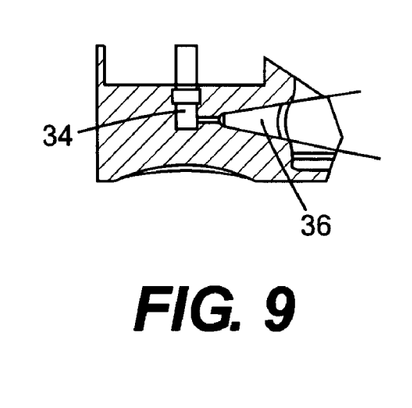
FIG. 9 is a detail view of the portion IX of FIG. 8.

Referring to FIGS. 7-9, there are shown three views of inner part 14 of inhaler system 10. Inner part 14 may be designed to be slidably received within outer part 12 and thus is slightly smaller than outer part 12 so that inner part 14 fits within outer part 12. Inner part 14 forms a compartment 20 for receiving a canister which may contain medication. Inner part 14 also includes a handle 30 which can be formed by, for example, texturing a portion of the surface of inner part 14, as shown in FIG. 7. Other forms of suitable handles 30 may be employed, such as an indentation in part of the surface, an attached structure suitable for grasping, etc. Handle 30 is employed by the user to move inner part 14 from the closed position of FIGS. 1-3 wherein most of inner part 14 is located within outer part 12, to the open position of FIGS. 10-12, wherein at least a substantial portion of inner part 14 protrudes from outer part 12 sufficiently to allow insertion of a canister into compartment 20 of inner part 14 via tapered opening 22.

Also part of inner part 14 is nozzle assembly 32. Nozzle assembly 32 includes a nozzle inlet 34 and a nozzle outlet 36. Nozzle inlet 34 is designed for fluid connection to a canister to dispense medication from the canister. Nozzle outlet 36 is in fluid communication with nozzle inlet 34 and directs fluid from nozzle inlet 34 into chamber 18 of inhaler system 10. Any conventional, suitable nozzle assembly 32 may be employed. Optionally, nozzle inlet 34 includes a conventional universal connector, not shown, that it is adapted to attach to a variety of different canisters.

In operation, a canister is operatively connected to nozzle inlet 34, in a conventional manner. A portion of the canister will protrude from compartment 20 through tapered opening 22. The user will depress the protruding portion of the canister to dispense a metered dose of medication from the canister to the nozzle inlet 34. The metered dose of medication then proceeds to chamber 18 via nozzle outlet 36.

Figure 13A:
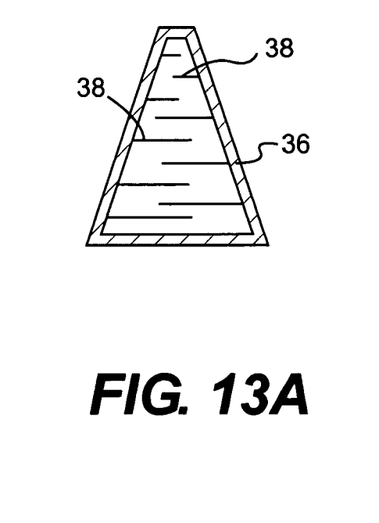
FIGS. 13A-13B are cross-sectional views of nozzle outlets including fluid mixing structure.
Figure 13B:
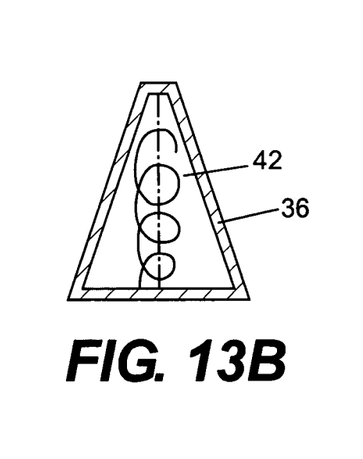

In an optional embodiment, nozzle outlet 36 includes structure for mixing the medication with air as it flows through nozzle outlet 36. Such structure may include, for example, a series of baffles, or a swirler shaped, for example, like a screw. The medication is forced through the mixing structure to chamber 18 to provide intimate mixing of air and medication to thereby entrain or disperse a greater amount of medication in air in chamber 18, than would be entrained or dispersed without a mixing structure. One suitable structure of nozzle outlet 36, including a series of baffles 38, is shown, for example, in FIG. 13A. A suitable swirler 42 included in nozzle outlet 36 is depicted in FIG. 13B. In one embodiment, the swirler 42 may be mounted for rotational movement about an axis to enhance mixing of the medication with air. Alternatively, baffles 38 or swirler 42 can be located in nozzle inlet 34, nozzle outlet 36, as shown, both locations, or combinations of baffles 38 and one or more swirlers 42 may also be employed. One suitable swirler 42 is available from Amici.

Figure 11:
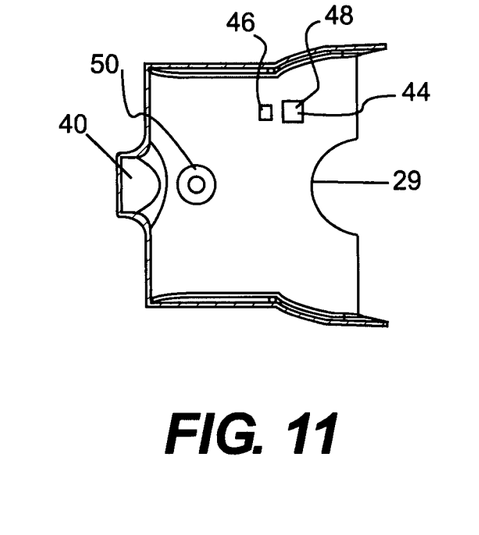
FIG. 11 is a horizontal plane cross-sectional view of the outer part of FIG. 10.

In another optional embodiment, inhaler system 10 may be provided with a counter 44, shown schematically in FIG. 11.

Counter 44 may include a button 46 and an indicator 48 to allow the user to keep track of the number of doses dispensed from a particular canister. Since most conventional canisters are designed to dispense a predetermined number of metered doses, and are not provided with a means to indicate how much medication remains in the canister, keeping track of the number of doses dispensed may be the only reliable way to determine when a particular medication canister is empty. Depression of button 46 would increment indicator 48 to indicate the number of doses. Indicator 48 can be any suitable indicator such as a digital display.

In another optional embodiment, inhaler system 10 may include a flow meter 50, shown schematically in FIG. 11. Any suitable, conventional flow meter 50 may be employed. For example, a telescoping flow meter 50 can be used in conjunction with a valve between chamber 18 and mouthpiece 40 to monitor peak flow of fluid into mouthpiece 40. The flow meter 50 can be used to ensure flow of medication to the patient, as well as to provide the patient with an indication as to whether sufficient inhalation pressure is being exerted by the patient on the mouthpiece 40 during inhalation of the medication/air mixture. This can be an important indication since higher peak flow rates will tend to reduce deposition of medication in the mouth or oropharyngeal area of the patient.

Figure 10:
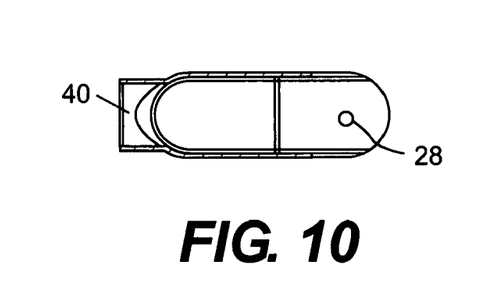
FIG. 10 is a sagittal plane cross-sectional view of one embodiment of the outer part of FIGS. 1-3.
Figure 12:
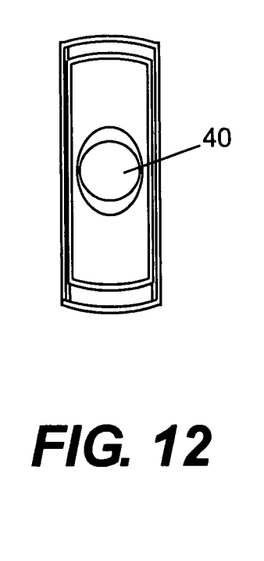
FIG. 12 is an end view of the outer part of FIG. 10.

Referring now to FIGS. 10-12, there are shown three views of outer part 12. Outer part 12 is adapted to receive inner part 14 at least partially within its structure and to form a chamber 18 in cooperation with inner part 14 for holding a metered dose of a mixture of medication and air for dispensing to a patient. For this purpose, outer part 12 includes a mouthpiece 40 or mouthpiece attachment. In one embodiment, outer part 12 includes a mouthpiece 40 as shown in FIGS. 10-12. Alternatively, a separate mouthpiece or mask could be provided, in which case, outer part 12 would be provided with a suitable mouthpiece attachment, not shown, to which the separate mouthpiece or mask could be attached. Mouthpiece 40 is in fluid communication with chamber 18 for delivery of a mixture of medication and air from chamber 18 to the mouth of a patient. Mouthpiece 40 or the mouthpiece connection can be formed as part of either outer part 12 or inner part 14, depending on the location on the inhaler system 10 at which the mouthpiece 40 or mouthpiece connection is to be placed, as well as the specific design of the outer and inner parts, 12, 14, respectively.

Chamber 18 may hold a volume of from about 130 to about 260 ml, more preferably from about 140 to about 180 ml, and most preferably, about 160-165 ml.

Outer part 12 also includes a recess 29 at a suitable location to allow the user to have access to handle 30 of inner part 14, when inner part 14 and outer part 12 are in the closed position of FIGS. 1-3. Recess 29 can also facilitate disassembly of inhaler system 10, for cleaning, as described below.

Figure 14:
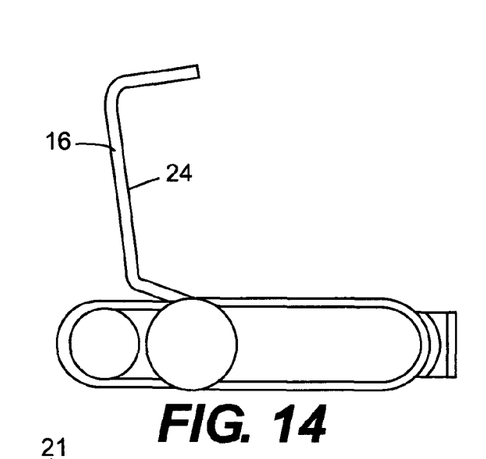
FIG. 14 is a side view of the inhaler system of FIGS. 1-3 in the open position.
Figure 15:
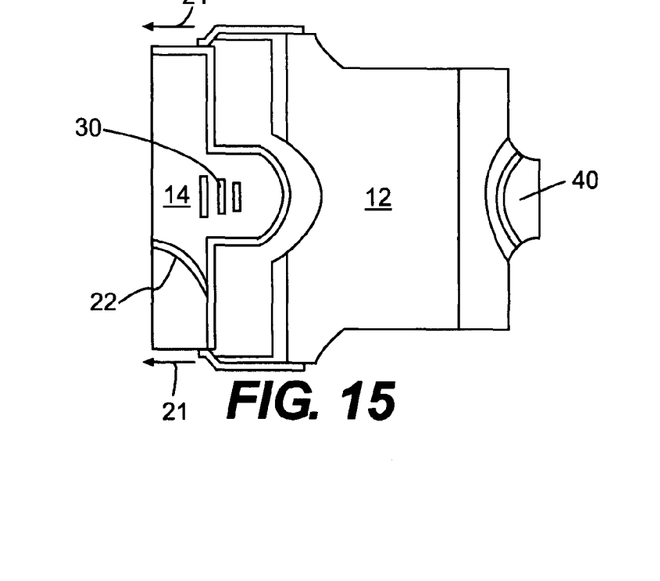
FIG. 15 is a bottom view of the inhaler system of FIGS. 1-3 in the open position.
Figure 16:
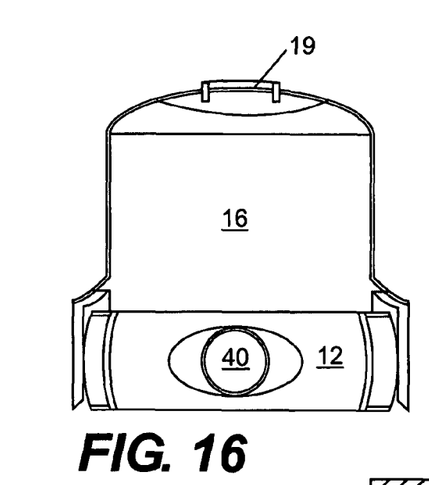
FIG. 16 is an end view of the inhaler system of FIGS. 1-3 in the open position.

Referring to FIGS. 14-16, there are shown three views of inhaler system 10 in the open position. The open position of inhaler system 10 is designed for insertion of a canister, as well as for use of inhaler system 10. Thus, when a user wishes to take a dose of medication, the user first opens cover 16, as shown in FIG. 14. The user then grasps inner part 14 by handle 30 and pulls inner part 14 in the direction of arrows 21 until it protrudes sufficiently from outer part 12, as shown in FIG. 15, that the user can depress a canister housed in compartment 20 of inner part 14. The user then places mouthpiece 40 in the user's mouth and depresses the canister to dispense a metered dose of medication to nozzle inlet 34. Medication is then mixed with air in nozzle outlet 36, optionally as described above and the medication/air mixture passes into chamber 18 for inhalation into the lungs of the user via mouthpiece 40. Once inhalation is completed, the user pushes inner part 14 back into outer part 12 and closes cover 16 to provide a small, easy to carry inhaler system 10 in the closed position of FIGS. 1-3. Another advantage of the device of the present invention is that the medication canister fits completely within the device and need not be removed from the device between doses of medication.

For cleaning, the inhaler system 10 can be easily disassembled into three distinct parts, outer part 12, inner part 14 and cover 16, which can then be cleaned, for example, by soaking the parts in denture cleaning solution, with antibacterial soap and water, or by any other suitable means. Cleaning of inhaler systems is important since medication tends to deposit on surfaces of the system and may degrade or provide a good location for bacteria or other organisms to grow. Thus, the easy disassembly of the present device is an important advantage of the invention. To make cleaning easier, it is possible to fabricate inhaler system 10 from easy to clean plastic materials, such as food grade plastics, or other, suitable conventional materials. Also, the use of clear plastic materials to fabricate inhaler system 10 would allow the user to see when the system requires cleaning.

Figure 17:
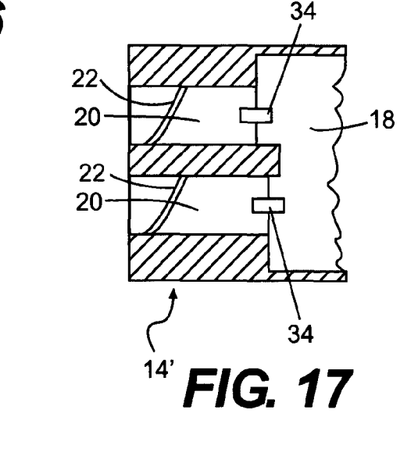
FIG. 17 is a cross-sectional view of an alternative embodiment of the inner part of the inhaler system.

An alternative embodiment of an inner part 14' is shown in FIG. 17. In this embodiment, inner part 14' includes at least two compartments 20 for housing two medication canisters. Compartments 20 may be the same or different. As shown in FIG. 20, two different compartments 20 are provided, each having different widths and depths. Each compartment is equipped with a nozzle inlet 34. Alternatively, only one of the plurality of compartments 20 need be fitted with an operative nozzle inlet 34, in which case other compartments could be used for storage of additional canisters of medication that can be inserted into the operative compartment 20 when dispensing of a metered dose of medication is desired.

Suitable changes must also be made to outer part 12 to provide two nozzle inlets 36 at locations corresponding to the nozzle inlets 34 of inner part 14'. Also, the inhaler system 10 may have to be slightly larger for the embodiment of FIG. 17, than for other embodiments, to accommodate the canisters' length while still providing a chamber 18 having a sufficient volume for the medication/air mixture. Such changes are within the ability of an ordinarily skilled person. This embodiment allows use of two different medications with the device without having to remove and replace a medication canister. Alternatively, two canisters of a single medication can be carried so that when one canister is depleted the new canister may be employed in order to prevent the patient from inadvertently running out of medication. Moreover, a separate mouthpiece specifically designed for infants can be attached to the various embodiments of the present invention if it is desired to use the device with an infant.

The foregoing detailed description has been provided for the purpose of illustration and description only and is not to be construed as limiting the invention in any way. The scope of the invention is to be determined from the claims appended hereto.

What is claimed is:

1. An inhaler system comprising:
   an outer part,
   an inner part adapted to be slidably received in said outer part and completely separable from said outer part by sliding the inner and outer parts relative to one another,
   said inner part comprising a compartment of sufficient size to receive a medication canister and a connector for operatively connecting to said medication canister for dispensing of a metered dose of medication from the canister, wherein a peripheral wall of said compartment defines an opening in said compartment for insertion of the medication canister and said peripheral wall has a shorter length at an outer portion of said inner part than at an inner portion of said inner part so as to accommodate medication canisters of different lengths and facilitate user access to the medication canister when located in said compartment, when said inner part is slidably received in said outer part, said inner and outer parts together form a housing that defines a chamber of sufficient volume to hold a metered dose of medication, said chamber being in fluid communication with said connector, said outer part including a mouthpiece or mouthpiece attachment location in fluid communication with said chamber for permitting inhalation of medication from said chamber via said mouthpiece or mouthpiece attachment location, and wherein said inner and outer parts slide relative to each other to move said inhaler system from a closed position to an open position to allow access to a medication canister located in said compartment without disengaging said inner part from said outer part.

2. An inhaler system as claimed in claim 1, wherein said connector is a universal connector.

3. An inhaler system as claimed in claim 1, further comprising a counter located on said housing for providing an indication of the number of metered doses dispensed from a canister.

4. An inhaler system as claimed in claim 1, further comprising a flow meter for providing an indication of a flow rate of fluid from said chamber to said mouthpiece or mouthpiece attachment location.

5. An inhaler system as claimed in claim 1, wherein said inhaler system further comprises mixing structure located between said connector and said chamber.

6. An inhaler system as claimed in claim 5, wherein said mixing structure comprises a plurality of baffles.

7. An inhaler system as claimed in claim 5, wherein said mixing structure comprises a swirler.

8. An inhaler system as claimed in claim 7, wherein said swirler is mounted for rotational movement about an axis of said swirler.

9. An inhaler system as claimed in claim 1, wherein said inhaler system further comprises a cover releasably attached to the said outer part.

10. An inhaler system as claimed in claim 9, wherein said cover includes a surface provided with information thereon.

11. An inhaler system as claimed in claim 9, wherein said cover is pivotally attached to said outer part for movement from a closed position to an open position without disengaging said cover from said outer part.

12. An inhaler system as claimed in claim 9, wherein said cover includes structure for covering the mouthpiece or mouthpiece attachment location when said cover is located in the closed position.

13. An inhaler system as claimed in claim 1, said inner and outer parts create a substantially airtight seal defining said chamber.

14. An inhaler system comprising:
an outer part,
an inner part adapted to be slidably received in said outer part and completely separable from said outer part by sliding the inner and outer parts relative to one another,
said inner part comprising a compartment of sufficient size to receive a medication canister and a connector for operatively connecting to said medication canister for dispensing of a metered dose of medication from the canister,
when said inner part is slidably received in said outer part, said inner and outer parts together form a housing that defines a chamber of sufficient volume to hold a metered dose of medication, said chamber being in fluid communication with said connector,
a mixing structure located between said connector and said chamber,
said outer part including a mouthpiece or mouthpiece attachment location in fluid communication with said chamber for permitting inhalation of medication from said chamber via said mouthpiece or mouthpiece attachment location,
a cover releasably and pivotally attached to the said outer part for movement from a closed position to an open position without disengaging said cover from said outer part, said cover covering said mouthpiece or mouthpiece attachment when said cover is in the closed position, and
wherein said inner and outer parts slide relative to each other to move said inhaler system from a closed position to an open position to allow access to a medication canister located in said compartment without disengaging said inner part from said outer part.

15. An inhaler system as claimed in claim 14, wherein said mixing structure comprises a structure selected from a plurality of baffles and a swirler mounted for rotational movement about an axis of the swirler.

16. An inhaler system as claimed in claim 15, wherein a peripheral wall of said compartment defines an opening in said compartment for insertion of the medication canister and said peripheral wall has a shorter length at an outer portion of said inner part than at an inner portion of said inner part so as to accommodate medication canisters of different lengths and facilitate user access to the medication canister when located in said compartment; and
said inner part further comprises a handle to facilitate sliding said inner and outer parts relative to each other to move said inhaler system between the closed position and the open position.

17. An inhaler system as claimed in claim 16, further comprising:
a flow meter for providing an indication of a flow rate of fluid from said chamber to said mouthpiece or mouthpiece attachment location; and
a counter located on said housing for providing an indication of the number of metered doses dispensed from a canister.

18. An inhaler system as claimed in claim 17, wherein said connector is a universal connector.

19. An inhaler system as claimed in claim 18, wherein when said inner part is slidably received in said outer part, said inner and outer parts create a substantially airtight seal defining said chamber.

20. An inhaler system as claimed in claim 14, wherein said connector is a universal connector.

\* \* \* \* \*